United States Patent

Klaus et al.

Patent Number: 5,216,148
Date of Patent: Jun. 1, 1993

[54] CARBOXAMIDES AND ANILIDES

[75] Inventors: Michael Klaus, Weil am Rhein, Fed. Rep. of Germany; Peter Mohr, Basel, Switzerland

[73] Assignee: Hoffmann-La Roche Inc., Nutley, N.J.

[21] Appl. No.: 842,662

[22] Filed: Feb. 27, 1992

[30] Foreign Application Priority Data

Mar. 21, 1991 [CH] Switzerland .......................... 863/91

[51] Int. Cl.$^5$ .................. C07D 223/16; C07D 243/12; C07D 215/22; C07D 209/34
[52] U.S. Cl. ...................... 540/517; 540/460; 540/523; 546/158; 548/486
[58] Field of Search ...................... 540/460, 517, 523; 546/158

[56] References Cited

U.S. PATENT DOCUMENTS

| 4,985,448 | 1/1991 | Zilch et al. | 548/411 |
| 5,037,825 | 8/1991 | Klaus et al. | 549/49 |

FOREIGN PATENT DOCUMENTS

| 327986 | 8/1989 | European Pat. Off. | 548/411 |
| 350846 | 1/1990 | European Pat. Off. | 549/32 |

Primary Examiner—Robert T. Bond
Attorney, Agent, or Firm—George M. Gould; William H. Epstein; Patricia S. Rocha

[57] ABSTRACT

Described herein are compounds of the formula

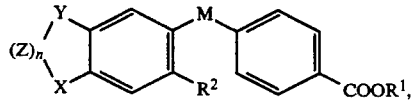

wherein
$R^1$ signifies hydrogen, lower-alkyl or a cation;
$R^2$ signifies hydrogen, lower-alkyl, lower-alkoxy or halogen;
M signifies —CONH— or —NHCO—;
X and Y are each independently selected from the group consisting of >CR$^3$R$^4$ and —CONR$^5$—;
Z signifies >CR$^6$R$^7$;
$R^3$, $R^4$, $R^6$ and $R^7$ are each independently selected from the group consisting of hydrogen and lower-alkyl;
$R^5$ signifies alkyl; and
n signifies 0, 1 or 2;

provided that at least one of X or Y is —CONR$^5$— which is bonded to the phenyl ring via the N atom.

These compounds are useful in the treatment and prophylaxis of neoplasms, dermatoses and aging of the skin.

9 Claims, No Drawings

CARBOXAMIDES AND ANILIDES

BACKGROUND OF THE INVENTION

The present invention is concerned with novel carboxamides and anilides of the formula

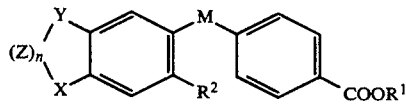

wherein
$R^1$ signifies hydrogen, lower-alkyl or a cation;
$R^2$ signifies hydrogen, lower-alkyl, lower-alkoxy or halogen;
M signifies —CONH— or —NHCO—;
X and Y are each independently selected from the group consisting of $>CR^3R^4$ and —$CONR^5$—;
Z signifies $>CR^6R^7$;
$R^3$, $R^4$, $R^6$ and $R^7$ are each independently selected from the group consisting of hydrogen and lower-alkyl;
$R^5$ signifies alkyl; and
n signifies 0, 1 or 2;
provided that at least one of X or Y is —$CONR^5$— which is bonded to the phenyl ring via the N atom.

These compounds are useful in the treatment and prophylaxis of neoplasms, dermatoses and aging of the skin.

The invention is also concerned with a process for the manufacture of compounds of formula I, pharmaceutical preparations based on these compounds and the use of these compounds in the treatment and prophylaxis of neoplasms, dermatoses and aging of the skin, as well as in the manufacture of pharmaceutical preparations for the treatment and prophylaxis of such disorders.

DETAILED DESCRIPTION OF THE INVENTION

As used in this application, the term "lower", as in "lower-alky" and "lower-alkoxy," relates to groups with 1–6 carbon atoms. Alkyl and alkoxy groups can be straight-chain or branched, such as methyl, ethyl, propyl, isopropyl, butyl, sec.-butyl or tert.-butyl and, respectively, methoxy, ethoxy, propoxy, isopropoxy, n-butoxy, sec.- or tert.-butoxy. Halogen includes fluorine, chlorine, bromine and iodine.

The carboxylic acids of formula I can form salts with bases. Preferred bases for such salt formation include alkali metal hydroxides, preferably sodium hydroxide or potassium hydroxide. These salts are also an object of the present invention.

A preferred group of compounds of formula I comprises those in which n is 1 or 2, most preferably 2. Also preferred are compounds of formula I in which one of the residues X or Y represents —$CONR^5$— and the other represents $>CR^3R^4$. $R^1$ and $R^2$ are preferably hydrogen; $R^3$ and $R^4$ are preferably lower-alkyl, especially methyl and ethyl; $R^5$ is preferably methyl; and $R^6$ and $R^7$ are preferably hydrogen.

Compounds of formula I can be manufactured by reacting a compound of the formula

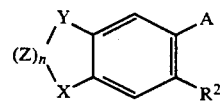

with a compound of the formula

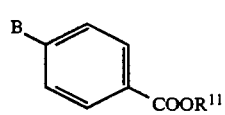

In formulas II and III, X, Y, Z, n and $R^2$ are as defined above, A is a carboxyl group or a reactive derivative thereof and B is an amino group, or A is an amino group and B is a carboxyl group or a reactive derivative thereof, and $R^{11}$ is lower alkyl.

Alternatively, compounds of formula I can be manufactured by reacting a compound of the formula

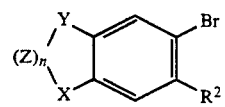

wherein X, Y, Z, n and $R^2$ are as defined above; with a compound of the formula

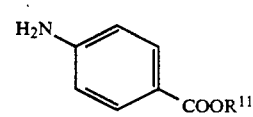

wherein $R^{11}$ is lower-alkyl; in the presence of carbon monoxide, a transition metal and an amine. It may also be desirable to saponify the ester group $COOR^{11}$ and isolate the resulting acid or salt.

The reaction of a compound of formula II with a compound of formula III can be carried out according to methods known in the art for the acylation of amines. Preferably, a compound of formula II in which A is a carboxylic acid halide group, e.g. the group —COCl, is reacted with a compound of formula III in which B is —$NH_2$ to give a compound of formula I in which M is —CONH—. Alternatively, an amine of formula II is reacted with a carboxylic acid halide of formula III to give a compound of formula I in which M is —NHCO—.

These acylations are conveniently carried out in the presence of a base, e.g. an organic base such as pyridine.

The reaction of a compound of formula IV and a compound of formula V can be carried out according to methods known in the art. For example, nickel and palladium, preferably palladium, are useful transition metal catalysts for the reaction of compounds of formula IV and V with carbon monoxide. Preferred amines include tertiary amines such as tributylamine and triethylamine, which can simultaneously serve as the solvent for the reaction partners. If desired, an additional inert organic solvent such as dimethylformamide or dimethylacetamide can be used. These reactions are conveniently carried out at an elevated temperature, e.g. at 50°–100° C., and under an elevated carbon monoxide pressure, e.g. a pressure of 5–20 bar.

A carboxylic acid ester of formula I can be hydrolyzed to the coresponding carboxylic acid by methods known to those skilled in the art, e.g. by treatment with alkalies, especially by treatment with aqueous alcoholic sodium hydroxide or potassium hydroxide, at a temperature ranging from room temperature to the boiling point of the reaction mixture. The carboxylic acids of formula I can be isolated in free form or can be converted into a pharmaceutically usable salt, e.g. the Na or K salt.

The compounds of formulae II and III which are used as starting materials for the manufacture of the compounds of formula I, insofar as they are not known or specifically described hereinafter, can be prepared by methods analogous to known methods or to methods described hereinbelow.

The compounds of formula I and their physiologically compatible salts are pharmacodynamically valuable compounds. They can be used for the topical and systemic therapy of benign and malignant neoplasms, of premalignant lesions and also for the systemic and topical prophylaxis of these conditions.

These compounds are also suitable for the topical and systemic therapy of acne, psoriasis and other dermatoses which are accompanied by an intensified or pathologically altered cornification, and also of inflammatory and allergic dermatological conditions as well as of light-damaged (e.g., U.V. or photo-damaged) (aging) skin. Further, the compounds of formula I can also be used for the control of mucous membrane disorders with inflammatory, degenerative or metaplastic changes.

The compounds of formula I can also be used for the treatment of inflammatory, allergic, rheumatic and immuno-logical disorders of a wide variety of organs. Examples of such disorders are: primarychronic polyarthritis, spondylarthritis ancylopoetica, osteoarthritides, arthritides and arthroses; eczemas, atopic dermatitis, allergic rhinitis, bronchial asthma; and autoimmune disorders such as e.g. lupus erythematosus and Reiter's syndrome. In contrast to retinoids, the present compounds have no teratogenic effect in limb bud cell cultures (Arch. Toxicol. 60 (1987) 403-414).

The activity of the compounds of formula I in the treatment of acne can be tested, e.g., in vitro on the basis of the anti-proliferative effects on human sebocytes (see method described in J. Invest. Dermatol. 90 (1988) 544) or by their influence on the sebaceous glands of the ear of the male Syrian hamster (see method described in J. Invest. Dermatol. 81 (1983) 43, and 68 (1977) 171). In the inhibition of sebocyte proliferation the tested compounds of formula I exhibited inhibitory activity ($ED_{50}$) in concentrations of 0.1-1 $\mu$mol.

In the hamster ear test, the compounds of formula I were found to reduce the sebaceous gland size by 20 to 40% in dosages of 0.5 to 10 mg/kg.

The compounds of formula I and their salts can be incorporated in pharmaceutical preparations. These preparations may be administered enterally, parenterally or topically. Preparations in the form of tablets, capsules, dragees, syrups, suspensions, solutions and suppositories are suitable for enteral administration. Preparations in the form of infusion solutions or injection solutions are suitable for parenteral administration.

The dosages in which the preparations are administered vary according to the mode of use and route of administration, as well as according to the requirements of the patients. The exact dosage can be ascertained by one skilled in the art taking into consideration the foregoing variables. For example, in the case of oral administration, adult dosages of about 0.1 mg/kg to about 100 mg/kg, preferably 0.5 mg/kg to about 50 mg/kg per day are recommended.

The pharmaceutical preparations according to the present invention can be administered in a single dosage or in several dosages. Capsules containing about 5-500 mg of active ingredient are a preferred administration form.

These preparations can also contain inert additives, as well as other pharmacodynamically active ingredients. Tablets or granulates can contain, inter alia, a series of binders, fillers, carriers or diluents. Liquid preparations can be present, for example, in the form a sterile water-miscible solution. Capsules can contain a filler or thickener in addition to the active ingredient. Furthermore, flavour-improving additives as well as substances usually used as preserving, stabilizing, moisture-retaining and emulsifying agents, salts for varying the osmotic pressure, buffers and other additives can be present.

The previously mentioned carrier materials and diluents can consist of organic or inorganic substances, e.g. water, gelatine, lactose, starch, magnesium stearate, talc, gum arabic, polyalkylene glycols and the like. It is understood, of course, that all adjuvants used in the manufacture of the preparations are non-toxic.

For topical use the active ingredients are conveniently used in the form of salves, tinctures, creams, solutions, lotions, sprays, suspensions and the like. Salves and creams as well as solutions are preferred. These preparations intended for topical use can be prepared by mixing the compounds of formula I or their salts as active ingredients with inert solid or liquid carriers which are usual in such preparations and which are suitable for topical treatment. Solutions for topical use, including salves, creams, lotions and sprays, contain from about 0.1% to about 5%, preferably from about 0.3% to about 2%, of a compound of formula I as the active ingredient If desired, an antioxidant, e.g. tocopherol, N-methyl-$\gamma$-tocopheramine, t-butyl-hydroxyanisole or t-butyl-hydroxytoluene, can be admixed with the preparations.

The following examples are presented by way of illustration and not as a limitation.

EXAMPLE 1

A. A solution of 25.0 g of 4,4-dimethyltetralone in 180 ml of glacial acetic acid was treated with 15.8 g of sodium azide, heated to 80° C. and the solution was treated with 25 ml of conc. sulphuric acid within 1 hour. Thereafter, the reaction mixture was stirred for a further 30 minutes and then poured into a mixture of ice and conc. sodium hydroxide solution. Extraction with sodium acetate, washing with sodium chloride solution, drying and evaporation yielded 32 g of a crude product which was processed immediately.

8.85 g of sodium hydride (about 55%) were suspended in 100 ml of dimethylformamide under argon. After cooling to 0° C. a solution of 32 g of the previously obtained crude product in 100 ml of dimethylformamide was added and the mixture was stirred for 1 hour. Thereafter, 15.8 ml of methyl iodide were added and the cooling bath was removed. After the strongly exothermic reaction subsided, the mixture was poured on to ice, extracted with diethyl ether, washed with sodium chloride, dried and evaporated. Flash chromatography on silica gel (petroleum ether/ethyl acetate 7:3) yielded 16.0 g of pure 2,3,4,5-tetrahydro-1,5,5-trimethyl-2-oxo-1H-1-benzazepine as a colourless oil.

B. 2.0 ml of 65% nitric acid were cautiously added dropwise to 7.1 ml of acetic anhydride at 0° C. This solution was added to a solution of 3.14 g of 2,3,4,5-tetrahydro-1,5,5-trimethyl-2-oxo-1H-1-benzazepine in 9.0 ml of acetic anhydride and 2.8 ml of glacial acetic acid. The reaction mixture was left to stand at room temperature for 3 days and then poured on ice, washed in succession with water, soda solution and water, dried and evaporated. Recrystallization from ethyl acetate/hexane yielded 3.39 g of 2,3,4,5-tetrahydro-1,5,5-trimethyl-7-nitro-2-oxo-1H-1-benzazepine, 113°–115° C.

C. 3.33 g of the previously obtained nitro compound were dissolved in 190 ml of abs. ethanol and hydrogenated at normal pressure over 230 mg of palladium/carbon (5%) at room temperature. After 1.5 hours the catalyst was filtered off and the solvent was removed under reduced pressure. There were obtained 2.92 g of 7-amino-2,3,4,5-tetrahydro-1,5,5-trimethyl-2-oxo-1H-1-benzazepine, m.p. 119°–122° C.

D. The corresponding acid chloride was prepared from 2.86 g of monoethyl terephthalate by refluxing with 1.94 ml of SOCl$_2$ and, after careful drying, was dissolved in 25 ml of pyridine and treated dropwise under argon at 0° C. with a solution of 2.91 g of the amine obtained in paragraph C. in 12 ml of pyridine. After 30 minutes at room temperature the reaction mixture was poured into an ice/conc. hydrochloric acid solution and extracted with ethyl acetate. After washing with water, soda solution and water, drying and evaporation there were obtained 4.24 g of ethyl p-[(2,3,4,5-tetrahydro-1,5,5-trimethyl-2-oxo-1H-1-benzazepin-7-yl)carbamoyl]benzoate as colourless crystals, m.p. 224°–226° C. (from ethyl acetate).

EXAMPLE 2

A. To a lithium diisopropylamine solution, prepared at 0° C. from 26.4 ml of diisopropylamine and 116 ml of 1.6M n-butyl-lithium in hexane, in 220 ml of abs. tetrahydrofuran was added dropwise, after cooling to −78° C., a solution of 27.8 g of 2,3,4,5-tetrahydro-1-methyl-2-oxo-1H-1-benzazepine in 50 ml of abs. tetrahydrofuran. The reaction mixture was warmed to room temperature, thereafter again cooled to −78° C. and treated with 19.4 ml of methyl iodide. Thereafter, the cooling bath was removed and the reaction mixture was stirred for a further 30 minutes, poured on to ice/conc. hydrochloric acid, extracted with diethyl ether, washed with water and saturated sodium chloride solution, dried and evaporated. There were obtained 28.7 g of a crude product which was again alkylated in the manner previously described. The thus-obtained crude product was purified by flash chromatography on silica gel (petroleum ether/ethyl acetate 85:15) and yielded 18.1 g of pure 2,3,4,5-tetrahydro-1,3,3-trimethyl-2-oxo-1H-1-benzazepine as a colourless oil.

B. A solution of 18.0 g of 2,3,4,5-tetrahydro-1,3,3-trimethyl-2-oxo-1H-1-benzazepine in 250 ml of methylene chloride was treated with 2.0 g of iron powder and thereafter dropwise with 5.83 ml of bromine in 30 ml of methylene chloride. The reaction mixture was heated to reflux overnight, thereafter poured on to ice, extracted with diethyl ether, washed with sodium pyro- sulphite solution, water and saturated sodium chloride solution, dried and evaporated. Crystallization from ethyl acetate/n-hexane yielded 21.4 g of pure 7-bromo-2,3,4,5-tetrahydro-1,3,3-trimethyl-2-oxo-1H-1-benzazepine.

C. A solution of 3.7 g of the bromo compound obtained above in paragraph B in 80 ml of tetrahydrofuran was treated dropwise under argon at −78° C. with 9.5 ml of 1.6M n-butyllithium in hexane. After a reaction period of 15 minutes a vigorous CO$_2$ stream was conducted through the reaction mixture for 10 minutes, thereafter the reaction mixture was poured into an ice/conc. hydrochloric acid solution and extracted with ethyl acetate. For the further purification, the extract was extracted with 1N sodium hydroxide solution, the aqueous phase was adjusted to pH<1 with conc. hydrochloric acid and again extracted with ethyl acetate. The organic extract was washed with water and saturated sodium chloride solution, dried and evaporated. There were obtained 2.50 g of 2,3,4,5-tetrahydro-1,3,3-trimethyl-2-oxo-1H-1-benzazepin-7-yl-carboxylic acid, m.p. 240°–241° C. (from ethyl acetate).

D. 2.38 g of 2,3,4,5-tetrahydro-1,3,3-trimethyl-2-oxo-1H-1-benzazepin-7-yl-carboxylic acid were converted into the corresponding acid chloride by refluxing with 1.75 ml of thionyl chloride for 30 minutes, dissolved in 20 ml of abs. pyridine after careful drying and added dropwise at 0° C. to a solution of 1.50 g of ethyl 4-aminobenozate in 20 ml of abs. pyridine. After a reaction period of 1 hour at room temperature the reaction mixture was poured into an ice/conc. hydrochloric acid solution, extracted with ethyl acetate and the organic phase was washed in succession with water, 0.5N sodium hydroxide solution and saturated sodium chloride solution, dried and evaporated. There were obtained 2.95 g of pure ethyl-p-(2,3,4,5-tetrahydro-1,3,3-trimethyl-2-oxo-1H-1-benzazepine-7-carboxamido)benzoate, m.p. 169°–170° C. (from ethyl acetate).

EXAMPLE 3

A. 43.0 g of diethyl dimethylmalonate and thereafter 24.7 g of o-phenylenediamine were added to a sodium ethylate solution freshly prepared from 10.5 g of sodium and 400 ml of abs. ethanol under argon. The reaction mixture was heated continuously to 180° C. in the course of 2 hours, whereby ethanol was distilled off continuously. After cooling the dried residue was triturated with dilute hydrochloric acid, the precipitate was filtered off and washed with water and ethanol. After drying in a high vacuum there were obtained 30.2 g of 2,3,4,5-tetrahydro-3,3-dimethyl-2,4-dioxo-1H-1,5-benzodiazepine as a brownish powder, m.p.>270° C. This product was added portionwise under argon to 17.0 g of sodium hydride (about 55%) in 300 ml of abs. dimethylformamide at 0° C. After the exothermic reaction had faded away 27.6 ml of methyl iodide were added and the reaction mixture was warmed to room temperature. Thereafter, it was poured on ice and extracted with ethyl acetate. The extract was washed with water and saturated sodium chloride solution, dried and concentrated up to crystallization. There were obtained 29.5 g of 2,3,4,5-tetrahydro-1,3,3,5-tetramethyl-2,4-dioxo-1H-1,5-benzodiazepine, m.p. 159°–160° C.

B. 1.0 g of iron powder and dropwise 6.65 ml of bromine were added to 15 g of the previously obtained benzodiazepinedione in 200 ml of methylene chloride. The reaction mixture was stirred at room temperature overnight, then again treated with 3.33 ml of bromine and 0.50 g of iron powder and left to react for a further 3 hours. Thereafter, the mixture was poured on ice, extracted with ethyl acetate, washed with pyrosulphite solution, water and saturated sodium chloride solution, dried and concentrated up to crystallization. There were obtained 10.9 g of 7-bromo-2,3,4,5-tetrahydro-1,3,3,5-tetramethyl-2,4-dioxo-1H-1,5-benzodiazepine, m.p. 194.5°–195° C.

C. A solution of 5.00 g of the previously obtained bromide in 200 ml of abs. tetrahydrofuran was treated dropwise under argon at −78° C. with 12.1 ml of 1.6M n-butyllithium in hexane. After 30 minutes the cooling bath was removed and a vigorous $CO_2$ stream was conducted in for 10 minutes. Thereafter, the reaction mixture was poured into an ice/conc. hydrochloric acid solution, extracted with ethyl acetate, the extract was washed with water, dried and evaporated. There were obtained 2.71 g of 2,3, 4,5-tetrahydro-1,3,3,5-tetramethyl-2,4-dioxo-1H-1,5-benzodiazepin-7-yl-carboxylic acid, m.p. >275° C.

D. The acid chloride was prepared from 3.17 g of the carboxylic acid obtained in paragraph C above by refluxing with 2.6 ml of thionyl chloride for 30 minutes. After careful drying the acid chloride was dissolved in 30 ml of abs. pyridine and added dropwise under argon at 0° C. to a solution of 1.98 g of ethyl 4-aminobenzoate in 15 ml of abs. pyridine. The reaction mixture was left to react at room temperature for 30 minutes, thereafter poured into an ice/conc. hydrochloric acid solution, extracted several times with a large amount of ethyl acetate, the extract was washed with water, dried and evaporated. There were obtained 3.98 g of ethyl p-(2,3,4,5-tetrahydro-1,3,3,5-tetramethyl-2,4-dioxo-1H-1,5-benzodiazepine-7-carboxamido)benzoate, m.p. 278°–279° C.

EXAMPLE 4

A. 1.3 ml of nitric acid (65%) were cautiously added dropwise at 0° C. to 5.1 ml of acetic anhydride. The solution was added to a solution of 3.00 g of 2,3,4,5-tetrahydro-1,3,3,5-tetramethyl-2,4-dioxo-1H-1,5-benzodiazepine in 6.5 ml of acetic anhydride and 2.1 ml of glacial acetic acid. The reaction mixture was left to stand at room temperature for 3 days, filtered, the residue was washed thoroughly with water, dried and recrystallized from ethanol. There were obtained 2.11 g of 2,3,4,5-tetrahydro-1,3,3,5-tetramethyl-7-nitro-2,4-dioxo-1H-1,5-benzodiazepine, m.p. 224°–225° C.

B. 2.35 g of the nitro compound obtained in paragraph A were suspended in 100 ml of abs. ethanol and, after the addition of 0.5 g of palladium/carbon (5%), hydrogenated overnight at room temperature and normal pressure. After filtration over a filter aid, washing and evaporation of the filtrate the residue was digested in diethyl ether and yielded 2.12 g of 7-amino-2,3,4,5-tetrahydro-1,3,3,5-tetramethyl-2,4-dioxo-1H-1,5-benzodiazepine, m.p. 221°–222° C.

C. 1.58 g of monoethyl terephthalate were converted by refluxing with 1.5 ml of thionyl chloride into the corresponding acid chloride which, after careful drying, was dissolved in 10 ml of abs. pyridine and added dropwise at 0° C. to a solution of 2.01 g of the amino compound prepared in paragraph B above in 15 ml of abs. pyridine. After a reaction period of 30 minutes at room temperature the mixture was poured into an ice/conc. hydrochloric acid solution, extracted with ethyl acetate, the extract was washed with water and saturated sodium chloride solution, dried and evaporated. Recrystallization from ethyl acetate yielded 2.89 g of ethyl p-[(2,3,4,5-tetrahydro-1,3,3,5-tetramethyl-2,4-dioxo-1H-1,5-benzodiazepin-7-yl)carbamoyl]benzoate, m.p. >270° C.

EXAMPLE 5

Analogous to Example 1, 7-amino-2,3,4,5-tetrahydro-1,5,5-trimethyl-2-oxo-1H-1-benzazepine was reacted with p-ethoxycarbonylbenzoyl chloride to yield ethyl p-[(2,3,4,5-tetrahydro-1,3,3-trimethyl-2-oxo-1-benzazepin-7-yl)carbamoyl]benzoate, m.p. 183°–184° C.

EXAMPLE 6

Analogous to Example 1, from 7-amino-2,3,4,5-tetrahydro-1-methyl-2-oxo-1H-1-benzazepine was reacted with p-ethoxycarbonylbenzoyl chloride to yield ethyl p-[(2,3,4,5-tetrahydro-1-methyl-2-oxo-1H-1-benzazepin-7-yl)carbamoyl]benzoate, m.p. 184°–185° C.

EXAMPLE 7

1.00 g of ethyl p-[(2,3,4,5-tetrahydro-1,5,5-trimethyl-2-oxo-1H-1-benzazepin-7-yl)carbamoyl]benzoate in 75 ml of ethanol/water (2:1) was treated with 0.40 g of sodium hydroxide and the reaction mixture was stirred at room temperature overnight. Thereafter, it was poured on to ice/conc. hydrochloric acid, extracted with ethyl acetate, the extract was washed with saturated sodium chloride solution, dried and concentrated up to crystallization. There was obtained 0.79 g of p-[(2,3,4,5-tetra- hydro-1,5,5-trimethyl-2-oxo-1H-1-benzazepin-7-yl)carbamoyl]benzoic acid, m.p. >275° C.

EXAMPLE 8

The following compounds were prepared according to the procedure described above in Example 7:

p-[(2,3,4,5-Tetrahydro-1,3,3-trimethyl-2-oxo-1H-1-benzazepin-7-yl)carbamoyl]benzoic acid, m.p. 272°–273° C.;

p-[(2,3,4,5-tetrahydro-1-methyl-2-oxo-1H-1-benzazepin-7-yl)carbamoyl]benzoic acid, m.p. >270° C.;

rac-p-[(2,3,4,5-tetrahydro-1,3,5,5-tetramethyl-2-oxo-1H-1-benzazepin-7-yl)carbamoyl]benzoic acid, m.p. >250° C.; and p-[(2,3,4,5-tetrahydro-1,3,3,5-tetramethyl-2,4-dioxo-1H-1,5-benzodiazepin-7-yl)carbamoyl]benzoic acid, m.p. >270° C.

EXAMPLE 9

1.69 ml of 3N sodium hydroxide solution were added to 1.00 g of ethyl p-(2,3,4,5-tetrahydro-1,5,5-trimethyl-2-oxo-1H-1-benzazepin-7-carboxamido)benzoate in 10 ml of ethanol/tetrahydrofuran (1:1). The reaction mixture was stirred at room temperature for 3 days and thereafter poured on to ice/conc. hydrochloric acid and extracted with ethyl acetate. The extract was washed with saturated sodium chloride solution, dried and evaporated. Recrystallization from ethyl acetate yielded 0.81 g of p-(2,3,4,5-tetrahydro-1,5,5-trimethyl-2-oxo-1H-1-benzazepine-7-carboxamido)benzoic acid, m.p. >275° C.

EXAMPLE 10

The following compounds were prepared according to the procedure described above in Example 9:

p-(2,3,4,5-Tetrahydro-1,3,3,5-tetramethyl-2,4-dioxo-1H-1,5-benzodiazepine-7-carboxamido)benzoic acid, m.p. >270° C.;

p-(2,3,4,5-tetrahydro-1,3,3-trimethyl-2-oxo-1H-1-benzazepine-7-carboxamido)benzoic acid, m.p. 265°–266° C.;

p-(2,3,4,5-Tetrahydro-1-methyl-2-oxo-1H-1-benzazepine-7-carboxamido)benzoic acid, m.p. >270° C.;

rac-p-(2,3,4,5-tetrahydro-1,3-dimethyl-2-oxo-1H-1-benzazepine-7-carboxamido)benzoic acid, m.p. >280° C.;

rac-p-(2,3,4,5-tetrahydro-1,3-dimethyl-2-oxo-1H-1-benzazepine-8-carboxamido)benzoic acid, m.p. >260° C., and rac-p-(2,3,4,5-tetrahydro-1,3,5,5-tetramethyl-2-oxo-1H-1-benzazepine-7-carboxamido)benzoic acid, m.p. >250° C.

EXAMPLE 11

5 g of 7-bromo-3,4-dihydro-4,4-dimethyl-1-propyl-2(1H)-quinoline were dissolved in 40 ml of tributylamine and heated at 110° C. for 64 hours in an autocalve under a carbon monoxide pressure of 15 bar together with 15 g of ethyl p-aminobenzoate and 1 g of bis-triphenylphosphine-palladium dichloride. After cooling the mixture was filtered off from the catalyst, diluted with ethyl acetate and washed with ice-cold 3N hydrochloric acid and water and evaporated. The excess ethyl p-aminobenzoate was separated by chromatography (silica gel, eluent hexane/ethyl acetate 2:1). After recrystallization from ethyl acetate/hexane there were obtained 5.2 of ethyl p-(1-propyl-1,2,3,4-tetrahydro-4,4-dimethyl-2-oxo-7-quinolineboxamido)benzoate, m.p. 142°-144° C.

The 7-bromo-3,4-dihydro-4,4-dimethyl-1-propyl-2(1H)-quinoline used as the starting material was prepared as follows:

44.3 g of powdered potassium hydroxide were suspended in 200 ml of dimethyl sulphoxide and a solution of 50 g of N-(3-bromophenyl)-3,3-dimethyl-acrylamide in 300 ml of DMSO was added dropwise thereto. The mixture was stirred at room temperature for 1 hour and subsequently a solution of 50.3 g of propyl iodide in 200 ml of DMSO was added dropwise thereto. After 2 hours the reaction mixture was poured on to ice-water, extracted three times with ethyl acetate, the organic phase was washed several times with water, dried and evaporated. After filtration of the crude product over a silica gel column (eluent hexane/ethyl acetate 9:1), 58 g of N-propyl-N-(3-bromophenyl)-3,3-dimethyl-acrylamide were obtained as a yellow oil. This product was dissolved in 1.5 l of petroleum ether (high boiling). 52.3 g of aluminium chloride were added portionwise thereto while stirring and the mixture was subsequently heated at reflux for 2.5 hours. After cooling to 0°-5° C. 500 ml of ice-cold 1N hydrochloric acid were added dropwise thereto, the mixture was diluted with water and extracted several times with ether. The yellow oil obtained after drying and evaporation of the solvent was a 6:4 mixture of 5-bromo-3,4-dihydro-4,4-dimethyl-1-propyl-2(1H)-quinolinone. It was filtered over a silica gel column (eluent hexane/5% ethyl acetate) and taken up in a small amount of hexane. After seeding with the 7-bromo compound above, 12.2 g of pure 7-bromo-3,4-dihydro-4,4-dimethyl-1-propyl-2(1H)-quinolinone crystallized in the cold in colourless crystals, m.p. 50°-51° C.

EXAMPLE 12

37.2 g of 6-amino-3,4-dihydro-1,4,4-trimethyl-2(1H)-quinolinone were dissolved in 600 ml of pyridine and treated dropwise at room temperature with a solution of 43 g of 4-ethoxycarbonylbenzoyl chloride in 80 ml of tetrahydrofuran. After stirring at room temperature for 20 hours, the reaction mixture was poured on to ice-water, extracted several times with ethyl acetate, the organic phase was washed with cold 2N hydrochloric acid and water, dried and evaporated. Chromatography of the crude product (silica gel, eluent hexane/ethyl acetate 2:1, then ethyl acetate) and recrystallization from ethyl acetate/hexane, yielded 45.5 g of ethyl p-[(1,2,3,4-tetrahydro-1,4,4-trimethyl-2-oxo-6-quinolinyl)-carbamoyl]-benzoate, m.p. 197°-199° C.

The amino compound used as the starting material was prepared as follows:

50 g of 3,4-dihydro-1,4,4-trimethyl-2(1H)-quinolinone were dissolved in a mixture of 130 ml of acetic anhydride and 42 ml of acetic acid. A mixture of 105 ml of acetic anhydride and 29 ml of nitric acid 65% (prepared by the slow dropwise addition of the nitric acid to acetic anhydride at 0° C.) was cautiously added dropwise thereto at a temperature of 0°-5° C. After stirring the reaction mixture at room temperature for 3 days it was poured on ice-water, extracted with ethyl acetate and the organic phase was washed with cold dilute soda solution and water. The organic phase was then dried and evaporated yielding a brownish oil which crystallized upon trituration with a small amount of ether resulting in 42 g of 3,4-dihydro-1,4,4-trimethyl-6-nitro-2(1H)-quinolinone, m.p. 125°-127° C. (from ethyl acetate/hexane). This product was dissolved in 2.5 l of ethanol and hydrogenated over palladium/carbon (5%) under normal pressure at room temperature. The resulting crude product was then recrystallized from ethyl acetate/hexane yielding 34 g of 6-amino-3,4-dihydro-1,4,4-trimethyl-2(1H)-quinolinone, m.p. 126°-128° C.

EXAMPLE 13

40 g of ethyl p-[(1,2,3,4-tetrahydro-1,4,4-trimethyl-2-oxo-6-quinolinyl)carbamoyl]benzoate were suspended in 800 ml of ethanol and treated with a solution of 60 g of potassium hydroxide in 500 ml of water. A clear yellow solution was obtained after stirring at 50° C. for 3 hours. The reaction mixture was then evaporated to half (volume), diluted with ice-water and acidified with cold 2N hydrochloric acid. The precipitated carboxylic acid was filtered off under suction, washed with ice-water, dried at 80° C. in a high vacuum and recrystallized from 300 ml of acetic acid yielding 31.5 g of p-[(1,2,3,4-tetrahydro-1,4,4-trimethyl-2-oxo-6-quinolinyl)-carbamoyl]benzoic acid, m.p. 285°-287° C.

EXAMPLE 14

6 g of 3,4-dihydro-1,4,4-trimethyl-2-oxo-6-quinolinecarboxylic acid were treated with 20 ml of thionyl chloride and heated at reflux for 2 hours. After evaporation of the excess thionyl chloride the oily residue was dissolved in 10 ml of tetrahydrofuran and slowly added dropwise to a solution of 3.9 g of ethyl 4-aminobenzoate in 40 ml of pyridine. After stirring at room temperature for 20 hours the mixture was poured on to ice-water, extracted several times with ethyl acetate, the organic phase was washed with 2N hydrochloric acid, dried and evaporated. The oily crude product was purified by chromatography (silica gel, eluent hexane/ethyl acetate 2:1) and recrystallized from hexane/ethyl acetate to yield 4.9 g of ethyl p-(1,2,3,4-tetrahydro-1,4,4-trimethyl-2-oxo-6-quinolinecarboxamido)benzoate, m.p. 175°-177° C.

The 3,4-dihydro-1,4,4-trimethyl-2-oxo-6-quinolinecarboxylic acid used as the starting material was prepared as follows:

19.7 g of 6-acetyl-3,4-dihydro-1,4,4-trimethyl-2(1H)-quinolinone were dissolved in 100 ml of dioxan and added dropwise at 0° C. to an aqueous sodium hypobromite solution (prepared by the dropwise addition of 17.2 ml of bromine to a solution of 34.4 g of sodium hydroxide in 170 ml of water at 5° C.). After stirring at room temperature for 1 hour the reaction mixture consisted of two phases. The upper phase was discarded. The lower phase, after the addition of 20 ml of 10% sodium bisulphite solution, was acidified strongly by the addition of conc. hydrochloric acid. Repeated extraction of this lower layer with ethyl acetate yielded, after drying and evaporation, 17.9 g of ethyl p-(1,2,3,4-tetrahydro-1,4,4-trimethyl-2-oxo-6-quinolinecarboxamido)benzoate, m.p. 195°–197° C. (from methylene chloride/hexane).

EXAMPLE 15

Analogous to Example 13, of 2.6 g of ethyl p-(1,2,3,4-tetrahydro-1,4,4-trimethyl-2-oxo-6-quinolinecarboxamido)-benzoate were saponified with aqueous potassium hydroxide solution yielding, after recrystallization from acetic acid, 1.8 g of p-(1,2,3,4-tetrahydro-1,4,4-trimethyl-2-oxo-6-quinolinecarboxamido)benzoic acid, m.p. >315° C. (decomposition).

EXAMPLE 16

The following compounds were prepared according to the procedure described above in Example 11:
Ethyl p-(2,3,4,5-tetrahydro-1,5,5-trimethyl-2-oxo-1H-1-benzazepine-7-carboxamido)benzoate, m.p. 179°–180° C.;
ethyl p-(2,3,4,5-tetrahydro-1-methyl-2-oxo-1H-1-benzazepine-7-carboxamido)benzoate, m.p. 169°–170° C.;
ethyl rac-p-(2,3,4,5-tetrahydro-1,3-dimethyl-2-oxo-1H-1-benzazepine-8-carboxamido)benzoate, m.p. 223°–224° C., and
ethyl rac-p-(2,3,4,5-tetrahydro-1,3,5,5-tetramethyl-2-oxo-1H-1-benzazepine-7-carboxamido)benzoate, m.p. 185°–187° C.

EXAMPLE 17

Analogous to Example 13, 4 g of ethyl p-(1-propyl-1,2,3,4-tetrahydro-4,4-dimethyl-2-oxo-7-quinolinecarboxamido)benzoate were saponified with aqueous potassium hydroxide solution yielding after recrystallization from ethyl acetate/hexane, 2.7 g of p-(1-propyl-1,2,3,4-tetrahydro-4,4-dimethyl-2-oxo-7-quinolinecarboxamido)benzoic acid, m.p. 215°–217° C.

EXAMPLE 18

Analogous to Example 11, 7-bromo-1-decyl-3,4-dihydro-4,4-dimethyl-2(1H)-quinolinone was carbonylated using palladium catalysis, and reacted with ethyl p-amino-benzoate to yield, after recrystallization from diisopropyl ether, ethyl p-(1-decyl-1,2,3,4-tetrahydro-4,4-dimethyl-2-oxo-quinolinecarboxamido)benzoate, m.p. 95°–96° C.
The 7-bromo compound used as the starting material was prepared in analogy to Example 11 by the alkylation of N-(3-bromophenyl)-3,3-dimethyl-acrylamide with decyl bromide and subsequent ring closure with aluminium chloride. The isomeric bromo compounds resulting in the ring closure reaction were separated in this case by medium pressure chromatography on Merck prepared columns (eluent hexane/ethyl acetate 9:1). The 7-bromo-quinolinone compound had the smaller $R_F$ value and separated as a yellow oil.

EXAMPLE 19

Analogous to Example 13, ethyl p-(1-decyl-1,2,3,4-tetrahydro-4,4-dimethyl-2-oxo-quinolinecarboxamido)-benzoate was saponified with aqueous potassium hydroxide after recrystallization from ethyl acetate/hexane, p-(1-decyl-1,2,3,4-tetrahydro-4,4-dimethyl-2-oxo-quinolinecarboxamido)benzoic acid in white crystals, m.p. 161°–163° C.

EXAMPLE 20

Analogous to Example 11, 7-bromo-3,4-dihydro-1,4,4-trimethyl-2(1H)-quinolinone (m.p. 92°–94° C.) was carbonylated using palladium as a catalyst and thereafter reacted with ethyl p-aminobenzoate yielding, after recrystallization from methylene chloride/ether, ethyl p-(1,2,3,4-tetrahydro-1,4,4-trimethyl-2-oxo-7-quinolinecarboxamido)benzoate, m.p. 129°–130° C.

EXAMPLE 21

Analogous to Example 14, ethyl p-(1,2,3,4-tetrahydro-1,4,4-trimethyl-2-oxo-7-quinolinecarboxamido)benzoate was saponified with aqueous potassium hydroxide to yield, after recrystallization from ethyl acetate/hexane, p-(1,2,3,4-tetrahydro-1,4,4-trimethyl-2-oxo-7-quinolinecarboxamido)benzoic acid, m.p. 290°–292° C.

EXAMPLE 22

A. 14.62 g of 1-tetralone in 45 ml of methylene chloride were treated with 29.3 ml of trifluoroacetic anhydride and 8.40 g of ammonium nitrate while cooling with ice/NaCl. After 18 hours the mixture was poured cautiously into an ice/conc. NaOH solution and extracted with diethyl ether. The organic phase was washed in succession with soda solution and NaCl solution, dried and evaporated. Flash chromatography on silica gel (hexane/ethyl acetate=9/2) followed by recrystallization from hexane/ethyl acetate (1/1) yielded 7.87 g of 7-nitro-1-tetralone as brownish crystals of m.p. 104°–105° C.

B. 7.87 g of 7-nitro-1-tetralone from step A were placed in 55 ml of AcOH. Next, 7.0 g of $NaN_3$ were added and the resulting mixture was heated to 60° C. Then, 10.3 ml of conc. $H_2SO_4$ were slowly added dropwise. $N_2$ evolution took place and the temperature rose to 90° C. The reaction mixture was held at this temperature for ½ hour, then cooled and poured cautiously into an ice/28% NaOH solution. The mixture was extracted thoroughly with AcOEt, washed with a small amount of water, dried and evaporated. Flash chromatography on $SiO_2$ (hexane/ethyl acetate (1/1→pure ethyl acetate)) yielded 2.58 g of 2,3,4,5-tetrahydro-8-nitro-2-oxo-1H-1-benzazepine as brown crystals of m.p. 224°–226° C. besides regioisomeric lactam and unreacted starting material.

C. 2.58 g of 2,3,4,5-tetrahydro-8-nitro-2-oxo-1H-1-benzazepine dissolved in 30 ml of abs. dimethylformamide were added to 650 mg of 55% NaH in 20 ml of abs. dimethylformamide. The mixture was stirred for 1 hour, then cooled to 0° C. and 1.35 ml of methyl iodide were slowly added dropwise thereto. After 45 minutes the mixture was poured on ice, extracted with ethyl acetate, washed with NaCl solution, dried and evaporated. Flash chromatography on silica gel (hexane/ethyl acetate=1/1) yielded 2.46 g of 2,3,4,5-tetrahydro-1-methyl-8-nitro-2-oxo-1H-1-benzazepine as orange crystals of m.p. 151°–152° C.

D. 1.34 g of 2,3,4,5-tetrahydro-1-methyl-8-nitro-2-oxo-1H-1-benzazepine were dissolved in 90 ml of abs. ethanol and hydrogenated over 150 mg of 5% Pd/C at room temperature and under atmospheric pressure overnight. The mixture was filtered over a glass suction filter, evaporated and there were thus obtained 1.20 g of 8-amino-2,3,4,5-tetrahydro-1-methyl-2-oxo-1H-1-benzazepine as a pale rose solid.

E. The corresponding acid chloride was prepared from 1.37 g of monoethyl terephthalate by heating to reflux with 2.50 ml of $SOCl_2$. After careful drying this acid chloride was dissolved in 5 ml of abs. pyridine in a high vacuum and added dropwise at 0° C. to 1.22 g of 8-amino-2,3,4,5-tetrahydro-1-methyl-2-oxo-1H-1-benzazepine which had been placed in 5 ml of abs. pyridine. The mixture was left to react at room temperature for ½ hour and was then poured into an ice/conc. HCl solution. The mixture was extracted with ethyl acetate and washed in succession with soda solution and NaCl solution. Then, the extract was dried and concentrated in a vacuum to a volume of about 15 ml, whereby the product began to separate out. This direct crystallization yielded 1.90 g of ethyl p-[(2,3,4,5-tetrahydro-1-methyl-2-oxo-1H-1-benzazepine-8-yl)carbamoyl]benzoate as white crystals, m.p. 194.5°–195.5° C.

EXAMPLE 23

850 mg of ethyl p-[(2,3,4,5-tetrahydro-1-methyl-2-oxo-1H-1-benzazepine-8-yl)carbamoyl]benzoate were dissolved in 20 ml of tetrahydrofuran and 10 ml of ethanol and treated with 10 ml of 1.2N NaOH yielding a two-phase mixture. The mixture was stirred intensively at 35° C. for 8 hours, poured into an ice/conc. HCl solution and extracted thoroughly with ethyl acetate. The resulting product was washed with a small amount of NaCl solution, dryed, and concentrated, and the remaining residue was repeatedly boiled in ethyl acetate and dryed yielding 400 mg of p-[(2,3,4,5-tetrahydro-1-methyl-2-oxo-1H-1-benzazepin-8-yl)carbamoyl]benzoic acid as beige crystals, m.p. >270° C.

EXAMPLE 24

Analogous to Example 22, 4,4-dimethyl-1-tetralone was treated to yield ethyl p-[(2,3,4,5-tetrahydro-1,5,5-trimethyl-2-oxo-1H-1-benzazepin-8-yl)carbamoyl]benzoate as colourless crystals of m.p. 174°–175° C.

EXAMPLE 25

Analogous to Example 23, ethyl p-[(2,3,4,5-tetrahydro-1,5,5-trimethyl-2-oxo-1H-1-benzazepin-8-yl)carbamoyl]benzoate was treated to yield p-[(2,3,4,5-tetrahydro-1,5,5-trimethyl-2-oxo-1H-1-benzazepin-8-yl)carbamoyl]benzoic acid as colourless crystals of m.p. >250° C.

EXAMPLE 26

Analogous to Example 11, Pd-catalyzed amidation of 7-bromo-3,4-dihydro-4,4-dimethyl-1-butyl-2(1H)-quinolinone yielded ethyl p-(1-butyl-2,3,4,5-tetrahydro-5,5-dimethyl-2-oxo-1H-1-benzazepine-7-carboxamido)-benzoate as beige crystals of m.p. 137°–138° C.

EXAMPLE 27

Analogous to Example 9, ethyl p-(1-butyl-2,3,4,5-tetrahydro-5,5-dimethyl-2-oxo-1H-1-benzazepine-7-carboxamido)benzoate was reacted to yield p-(1-butyl-2,3,4,5-tetrahydro-5,5-dimethyl-2-oxo-1H-1-benzazepine-7-carboxamido)benzoic acid as colourless crystals of m.p. 269°–270° C.

EXAMPLE 28

The following compounds are prepared following the procedures described in the foregoing Examples:

Ethyl p-[(1,2,3,4-tetrahydro-1,4,4-trimethyl-2-oxo-7-quinolinyl)carbamoyl]benzoate;
p-[(1,2,3,4-tetrahydro-1,4,4-trimethyl-2-oxo-7-quinolinyl)carbamoyl]benzoic acid;
ethyl p-[(1,2,3,4-tetrahydro-1-propyl-4,4-dimethyl-2-oxo-7-quinolinyl)carbamoyl]benzoate;
p-[(1,2,3,4-tetrahydro-1-propyl-4,4-dimethyl-2-oxo-7-quinolinyl)carbamoyl]benzoic acid;
ethyl p-(1,3,3-trimethyl-2-oxo-5-indolinecarboxamido)benzoate;
ethyl p-[(1,3,3-trimethyl-2-oxo-5-indolinyl)carbamoyl]benzoate;
ethyl p-(1,3,3-trimethyl-2-oxo-6-indolinecarboxamido)benzoate;
ethyl p-[(1,3,3-trimethyl-2-oxo-6-indolinyl)carbamoyl]benzoate;
ethyl p-[(2,3,4,5-tetrahydro-1,3,3-trimethyl-2-oxo-1H-1-benzazepin-8-yl)carbamoyl]benzoate;
ethyl p-(2,3,4,5-tetrahydro-1-methyl-2-oxo-1H-1-benzazepine-8-carboxamido)benzoate;
p-(2,3,4,5-tetrahydro-1-methyl-2-oxo-1H-1-benzazepine-8-carboxamido)benzoic acid;
ethyl p-[(2,3,4,5-tetrahydro-1-n-butyl-5,5-dimethyl-2-oxo-1H-1-benzazepin-7-yl)carbamoyl]benzoate;
p-[(2,3,4,5-tetrahydro-1-n-butyl-5,5-dimethyl-2-oxo-1H-1-benzazepin-7-yl)carbamoyl]benzoic acid.

EXAMPLE A

Hard gelatine capsules can be produced as follows:

| | Ingredient | mg/capsules |
|---|---|---|
| 1. | Spray-dried powder containing 75% of compound of formula I | 200 |
| 2. | Sodium dioctylsulphosuccinate | 0.2 |
| 3. | Sodium carboxymethylcellulose | 4.8 |
| 4. | Microcrystalline cellulose | 86.0 |
| 5. | Talc | 8.0 |
| 6. | Magnesium stearate | 1.0 |
| | Total | 300 |

The spray-dried powder, which includes the active ingredient, gelatine and microcrystalline cellulose, is moistened with an aqueous solution of sodium carboxymethylcellulose and sodium dioctylsulphosuccinate and kneaded. In this powder, the average particle size of the active ingredient is about $<1\mu$ (measured by means of autocorrelation spectroscopy). The resulting mass is granulated, dried and sieved, and the granulate obtained is mixed with microcrystalline cellulose, talc and magnesium stearate. The powder is filled in size 0 capsules.

EXAMPLE B

Tablets can be produced as follows:

| | Ingredients | mg/tablet |
|---|---|---|
| 1. | Compound of formula I as a finely milled powder | 500 |
| 2. | Powd. lactose | 100 |
| 3. | White corn starch | 60 |
| 4. | Povidone K30 | 8 |
| 5. | White corn starch | 112 |
| 6. | Talc | 16 |

-continued

| | Ingredients | mg/tablet |
|---|---|---|
| 7. | Magnesium stearate | 4 |
| | Total | 800 |

The finely milled powder is mixed with lactose and a portion of the corn starch. The mixture is moistened with an aqueous solution of Povidone K30 and kneaded, and the resulting mass is granulated, dried and sieved. The resulting granulate is mixed with the remaining corn starch, talc and magnesium stearate and pressed into tablets of suitable size.

EXAMPLE C

Soft gelatine capsules can be prepared as follows:

| | Ingredients | mg/capsule |
|---|---|---|
| 1. | Compound of formula I | 50 |
| 2. | Triglyceride | 450 |
| | Total | 500 |

10 g of compound of formula I are dissolved in 90 g of medium-chain triglyceride with stirring, inert gasification and protection from light. This solution is processed as a capsule fill mass to soft gelatine capsules containing 50 mg of active ingredient.

EXAMPLE D

A lotion can be produced as follows:

| | Ingredients | |
|---|---|---|
| 1. | Compound of formula I finely milled | 3.0 g |
| 2. | Carbopol 934 | 0.6 g |
| 3. | Sodium hydroxide q.s. ad pH 6 | |
| 4. | Ethanol, 94% | 50.0 g |
| 5. | Demineralized water | ad 100.0 g |

The active ingredient, a compound of formula I, is incorporated into the 94% ethanol/water mixture with protection from light. Carbopol 934 is stirred in until gelling is complete and the pH value is adjusted with sodium hydroxide.

Other modifications of the above described embodiments of the invention which are obvious to those of skilled in the art are also intended to be within the scope of the following claims.

What is claimed is:

1. A compound of the formula

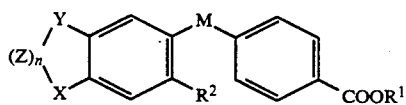

I wherein
$R^1$ signifies hydrogen, lower-alkyl or a cation;
$R^2$ signifies hydrogen, lower-alkyl, lower-alkoxy or halogen;
M signifies —CONH— or —NHCO—;
X and Y are each independently selected from the group consisting of $>CR^3R^4$ and —CONR$^5$—;
Z signifies $>CR^6R^7$;
$R^3$, $R^4$, $R^6$ and $R^7$ are each independently selected from the group consisting of hydrogen and lower-alkyl;
$R^5$ signifies alkyl; and
n signifies 0, 1 or 2;
provided that at least one of X or Y is —CONR$^5$— and is bonded to the phenyl ring via the N atom.

2. The compound of claim 1 in which n is 1 or 2.

3. The compound of claim 1 in which X is —CONR$^5$— and Y is $>CR^6R^7$.

4. The compound p-[(1,2,3,4-tetrahydro-1,4,4-trimethyl-2-oxo-6-quinolinyl)carbamoyl]benzoic acid.

5. A compound which is selected from the group consisting of:
ethyl p-[(2,3,4,5-tetrahydro-1,5,5-trimethyl-2-oxo-1H-1-benzazepin-7-yl)carbamoyl]benzoate;
ethyl p-(2,3,4,5-tetrahydro-1,3,3-trimethyl-2-oxo-1H-1-benzazepine-7-carboxamido)benzoate;
ethyl p-[(2,3,4,5-tetrahydro-1,3,3-trimethyl-2-oxo-1-benzazepin-7-yl)carbamoyl]benzoate;
ethyl p-[(2,3,4,5-tetrahydro-1-methyl-2-oxo-1H-1-benzazepin-7-yl)carbamoyl]benzoate;
p-[(2,3,4,5-tetrahydro-1,5,5-trimethyl-2-oxo-1H-1-benzazepin-7-yl)carbamoyl]benzoic acid;
p-[(2,3,4,5-tetrahydro-1,3,3-trimethyl-2-oxo-1H-1-benzazepin-7-yl)carbamoyl]benzoic acid;
p-[(2,3,4,5-tetrahydro-1-methyl-2-oxo-1H-1-benzazepin-7-yl)carbamoyl]benzoic acid;
rac-p-[(2,3,4,5-tetrahydro-1,3,5,5-tetramethyl-2-oxo-1H-1-benzazepin-7-yl)carbamoyl]benzoeic acid;
p-(2,3,4,5-tetrahydro-1,5,5-trimethyl-2-oxo-1H-1-benzazepine-7-carboxamido)benzoic acid;
p-(2,3,4,5-tetrahydro-1,3,3-trimethyl-2-oxo-1H-1-benzazepine-7-carboxamido)benzoic acid;
p-(2,3,4,5-tetrahydro-1-methyl-2-oxo-1H-1-benzazepine-7-carboxamido)benzoic acid;
rac-p-(2,3,4,5-tetrahydro-1,3-dimethyl-2-oxo-1H-1-benzazepine-7-carboxamido)benzoic acid;
rac-p-(2,3,4,5-tetrahydro-1,3-dimethyl-2-oxo-1H-1-benzazepine-8-carboxamido)benzoic acid;
ethyl p-[(1,2,3,4-tetrahydro-1,4,4-trimethyl-2-oxo-6-quinolinyl)carbamoyl]benzoate;
ethyl p-(1,2,3,4-tetrahydro-1,4,4-trimethyl-2-oxo-6-quinolinecarboxamido)benzoate;
p-(1,2,3,4-tetrahydro-1,4,4-trimethyl-2-oxo-6-quinolinecarboxamido)benzoic acid;
ethyl p-(2,3,4,5-tetrahydro-1,5,5-trimethyl-2-oxo-1H-1-benzazepine-7-carboxamido)benzoate;
ethyl p-(2,3,4,5-tetrahydro-1-methyl-2-oxo-1H-1-benzazepine-7-carboxamido)benzoate;
ethyl rac-p-(2,3,4,5-tetrahydro-1,3,5,5-tetramethyl-2-oxo-1H-1-benzazepine-7-carboxamido)benzoate;
ethyl p-(1-butyl-2,3,4,5-tetrahydro-5,5-dimethyl-2-oxo-1H-1-benzazepine-7-carboxamido)benzoate; and
p-(1-utyl-2,3,4,5-tetrahydro-5,5-dimethyl-2-oxo-1H-1-benzazepine-7-carboxamido)benzoic acid.

6. The compound of claim 1 in which Y is —CONR$^5$— and X is $>CR^6R^7$.

7. A compound which is selected from the group consisting of:
rac-p-(2,3,4,5-tetrahydro-1,3,5,5-tetramethyl-2-oxo-1H-1-benzazepine-7-carboxamido)benzoic acid;
ethyl p-(1-propyl-1,2,3,4-tetrahydro-4,4-dimethyl-2-oxo-7-quinolinecarboxamido)benzoate;
ethyl rac-p-(2,3,4,5-tetrahydro-1,3-dimethyl-2-oxo-1H-1-benzazepine-8-carboxamido)benzoate;
p-(1-propyl-1,2,3,4-tetrahydro-4,4-dimethyl-2-oxo-7-quinolinecarboxamido)benzoic acid;

ethyl p-(1-decyl-1,2,3,4-tetrahydro-4,4-dimethyl-2-oxoquinolinecarboxamido)benzoate;
p-(1-decyl-1,2,3,4-tetrahydro-4,4-dimethyl-2-oxoquinolinecarboxamido)benzoic acid;
ethyl p-(1,2,3,4-tetrahydro-1,4,4-trimethyl-2-oxo-7-quinolinecarboxamido)benzoate;
p-(1,2,3,4-tetrahydro-1,4,4-trimethyl-2-oxo-7-quinolinecarboxamido)benzoic acid;
ethyl p-[(2,3,4,5-tetrahydro-1-methyl-2-oxo-1H-1-benzazepin-8-yl)carbamoyl]benzoate;
p-[(2,3,4,5-tetrahydro-1-methyl-2-oxo-1H-1-benzazepin-8-yl)carbamoyl]benzoic acid;
ethyl p-[(2,3,4,5-tetrahydro-1,5,5-trimethyl-2-oxo-1H-1-benzazepin-8-yl)carbamoyl]benzoate; and
p-[(2,3,4,5-tetrahydro-1,5,5-trimethyl-2-oxo-1H-1-benzazepin-8-yl)carbamoyl]benzoic acid.

8. The compound of claim 1 in which X and Y are both —CONR$^5$—.

9. A compound which is selected from the group consisting of:
ethyl p-(2,3,4,5-tetrahydro-1,3,3,5-tetramethyl-2,4-dioxo-1H-1,5-benzodiazepine-7-carboxamido)benzoate;
ethyl p-[(2,3,4,5-tetrahydro-1,3,3,5-tetramethyl-2,4-dioxo-1H-1,5-benzodiazepin-7-yl)carbamoyl]benzoate;
p-[(2,3,4,5-tetrahydro-1,3,3,5-tetramethyl-2,4-dioxo-1H-1,5-benzodiazepin-7-yl)carbamoyl]benzoic acid; and
p-(2,3,4,5-tetrahydro-1,3,3,5-tetramethyl-2,4-dioxo-1H-1,5-benzodiazepine-7-carboxamido)benzoic acid.

* * * * *